(12) United States Patent
Schlemmer et al.

(10) Patent No.: US 10,870,006 B2
(45) Date of Patent: Dec. 22, 2020

(54) APPARATUS FOR APPLYING ELECTRIC PULSES TO LIVING MYOCARDIAL TISSUE

(71) Applicant: Max-Planck-Gesellschaft zur Foerderung der Wissenschaften e.V., Munich (DE)

(72) Inventors: Alexander Schlemmer, Goettingen (DE); Thomas Lilienkamp, Goettingen (DE); Sebastian Berg, Goettingen (DE); Ulrich Parlitz, Gleichen (DE); Stefan Luther, Goettingen (DE)

(73) Assignee: MAX-PLANCK-GESELLSCHAFT ZUR FOERDERUNG DER WISSENSCHAFTEN E.V., Munich (DE)

( * ) Notice: Subject to any disclaimer, the term of this patent is extended or adjusted under 35 U.S.C. 154(b) by 89 days.

(21) Appl. No.: 16/127,924

(22) Filed: Sep. 11, 2018

(65) Prior Publication Data
US 2019/0009089 A1 Jan. 10, 2019

Related U.S. Application Data

(63) Continuation of application No. PCT/EP2017/056021, filed on Mar. 14, 2017.

(30) Foreign Application Priority Data

Mar. 14, 2016 (EP) .................................. 16160234

(51) Int. Cl.
*A61N 1/36* (2006.01)
*A61N 1/362* (2006.01)
(Continued)

(52) U.S. Cl.
CPC ........ *A61N 1/3621* (2013.01); *A61B 5/04012* (2013.01); *A61B 5/0464* (2013.01);
(Continued)

(58) Field of Classification Search
CPC ........ A61N 1/365; A61B 5/0452; A61B 5/046
See application file for complete search history.

(56) References Cited

U.S. PATENT DOCUMENTS

| | | |
|---|---|---|
| 5,817,132 A | 10/1998 | Karagueuzian et al. |
| 6,775,571 B1 | 8/2004 | Kroll |
| (Continued) | | |

FOREIGN PATENT DOCUMENTS

| | | |
|---|---|---|
| CN | 102 284 138 B | 5/2014 |
| WO | 2012/172027 A2 | 12/2012 |

OTHER PUBLICATIONS

PCT International Search Report and Written Opinion in co-pending, related PCT Application No. PCT/EP2017/056021, dated Dec. 7, 2017.

(Continued)

*Primary Examiner* — Michael J D Abreu
(74) *Attorney, Agent, or Firm* — Thomas | Horstemeyer, LLP (57) ABSTRACT

An apparatus for applying at least one electric pulse to a living myocardial tissue comprises an input configured to receive an electric signal representing a present electric activity of the myocardial tissue; a signal processor configured to process the electric signal to calculate a present permutation value of the electric signal in the state space and to only output a control signal when the calculated present entropy value of the electric signal is lower than a predetermined entropy threshold value; a pulse generator configured to generate the at least one electric pulse in response to the control signal; and an output configured to output the at least one electric pulse to the myocardial tissue.

16 Claims, 4 Drawing Sheets

(51) Int. Cl.
*A61B 5/04* (2006.01)
*A61B 5/0464* (2006.01)
*A61N 1/05* (2006.01)
*A61N 1/365* (2006.01)
*A61B 5/00* (2006.01)
*A61N 1/37* (2006.01)

(52) U.S. Cl.
CPC ............ *A61B 5/4836* (2013.01); *A61N 1/056* (2013.01); *A61N 1/365* (2013.01); *A61N 1/3704* (2013.01)

(56) References Cited

U.S. PATENT DOCUMENTS

2009/0259266 A1* 10/2009 Zhang .................. A61B 5/0452
607/3

2010/0056940 A1* 3/2010 Moorman .............. A61B 5/412
600/518

OTHER PUBLICATIONS

Christoph Bandt and Bernd Pompe: Permutation entropy—a natural complexity measure for time series, Feb. 18, 2002.
Yinhe Cao at al: Detecting dynamical changes in time series using the permutation entropy, Physical Revue E 70, 046217 (2004).
E. Olofsson et al.: Permutation entropy of the electroencephalogram: A measure of anesthetic drug effect, British Journal of Anesthesia, Oct. 12, 2008.
J. Parlitz et al.: Classifying cardiac biosignals using ordinal patterns statistics and symbolic dynamics, Computers in Biology and Medicine 42 (2012) 319-327.
R. K. Tripathy et al.: Detection of shockable ventricular arrhythmia using variational mode decomposition, J Med Syst, Jan. 21, 2016.

* cited by examiner

APPARATUS FOR APPLYING ELECTRIC PULSES TO LIVING MYOCARDIAL TISSUE

CROSS REFERENCE

The present application is a continuation to international patent application PCT/EP2017/056021 filed on Mar. 14, 2017 and claiming priority to European patent application EP 16 160 234.7 filed on Mar. 14, 2016, both entitled "Apparatus for applying electric pulses to living myocardial tissue".

FIELD

The present invention relates to an apparatus for applying at least one electric pulse to a living myocardial tissue. More particular, the present invention relates to an apparatus for applying at least one electric pulse to a living myocardial tissue, the apparatus comprising an input receiving an electric signal representing a present electric activity of the myocardial tissue; a signal processor processing the electric signal to determine a present complexity measure of the electric signal, and to output a control signal; a pulse generator generating the at least one electric pulse in response to the control signal; and an output outputting the at least one electric pulse to the myocardial tissue. Particularly, the myocardial tissue may be the myocardium of a heart of a living animal or a human being.

BACKGROUND

WO 2012/172027 A2 discloses an apparatus for terminating a high frequency arrhythmic electric state of a biological tissue. The known apparatus comprises a determination unit which determines from an electric signal representative of the present electrical state of the biological tissue at least one dominant frequency. From the at least one dominant frequency the determination unit determines whether the present electric state of the biological tissue is a high frequency arrhythmic electric state. Further, the determination unit determines from the electric signal a dominance level indicative of how dominant the at least one dominant frequency is in the high frequency arrhythmic electric state. At a point in time at which the dominance level exceeds a predefined threshold value, the determination unit triggers an electric pulse generator to generate at least one series of electric pulses at intervals depending on the at least one dominant frequency. These electric pulses are applied to the biological tissue via at least one electrode connected to the pulse generator. The threshold value to which the dominance level is compared may be defined as a percentage of a previously recorded maximum value of the dominance level. For determining the dominance level, the determination unit compares the intensity of the electric signal at the dominant frequency with the intensity of the electric signal at at least one neighboring frequency. The electric pulse generator generates the electric pulses according to the LEAP (Low Energy Anti-fibrillation Pacing) concept at a comparatively low electric energy as compared to a standard defibrillation energy used for defibrillation by means of a single pulse providing an electric shock. WO 2012/172027 also discloses a concept of determining an optimum starting point for applying the electric pulses to the biological tissue based on monitoring a spectral complexity or spectral entropy of an electrocardiogram (ECG).

Christoph Bandt and Bernd Pompe: Permutation entropy—a natural complexity measure for time series, Feb. 18, 2002, see www.math.uni-bremen.de/zetem/DFG-Schwerpunkt/preprints/orig/bandt_ pompe_permutation.pdf, disclose permutation entropy as a complexity parameter for time series based on comparison of neighboring values. The permutation entropy is defined as a Shannon entropy of probabilities of ordinal patterns. Christoph Bandt and Bernd Pompe report results of applying the permutation entropy concept to a speech signal and to chaotic time series.

Yinhe Cao at al.: Detecting dynamical changes in time series using the permutation entropy, Physical Revue E 70, 046217 (2004) report the application of permutation entropy for clinically characterizing brain wave data from epileptic patients.

E. Olofsson et al.: Permutation entropy of the electroencephalogram: A measure of anesthetic drug effect, British Journal of Anesthesia, Oct. 12, 2008 report the application of the concept of permutation entropy on electroencephalograms (EEG) to monitor the effects of anesthetic drugs.

U. Parlitz et al.: Classifying cardiac biosignals using ordinal patterns statistics and symbolic dynamics, Computers in Biology and Medicine 42 (2012) 319-327 report an evaluation of the discriminative power of ordinal pattern statistics and symbolic dynamics, i.e. of the basics of permutation entropy, in comparison with established heart rate variability parameters applied to beat-to-beat intervals. Both sets of parameters were determined for ECG recordings from patients suffering from congestive heart failure and a healthy control group.

R. K. Tripathy et al.: Detection of shockable ventricular arrhythmia using variational mode decomposition, J Med Syst, Jan. 21, 2016 disclose variational mode decomposition (VMD) to decompose an ECG signal into a number of modes or subsignals for detection and classification of shockable ventricular arrhythmia including ventricular tachycardia (VT) and ventricular fibrillation (VF), and non-shockable ventricular arrhythmia episodes, including normal sinus rhythm, ventricular bigeminy, ventricular ectopic beats, and ventricular escape rhythm. The energy, Renyi entropy and permutation entropy of first three modes are evaluated, and these values are used as diagnostic features. Mutual information-based feature scoring is employed to select optimal sets of diagnostic features.

U.S. Pat. No. 6,775,571 B1 discloses a dynamic control of overdrive pacing based on a degree of randomness within a heart rate. The degree of randomness associated with the heart rate of a patient is determined based on an analysis of electrical heart signals. The degree of randomness is determined based on a degree of entropy or chaos dimensionality associated with the heart rate. If the degree of randomness falls below a threshold value, indicating that the heart rate may be too coherent, a warning signal is generated indicating a significant risk of onset of a tachyarrhythmia. To prevent the tachyarrhythmia from occurring, overdrive pacing is initiated or, if already initiated, the overdrive pacing is made more aggressive. Chaotic pacing may be performed to ensure a sufficient heart rate variability. The degree of entropy is determined using otherwise conventional entropy calculation techniques applied to the P-P intervals R-R intervals, or other appropriate indicators of the heart rate.

U.S. Pat. No. 5,817,132 A discloses an implanted defibrillator continuously monitoring a patient's heart to detect the presence of fibrillation and to repeatedly, automatically compute the approximate entropy of a series of data presenting the fibrillation heart at a moment in time. The first approximate entropy score that meets a predetermined relation with respect to a predetermined threshold value activates an energy delivery system to defibrillate the heart with a low level shock. A data processor receives heart data and repeatedly computes a scalar times series which is comprised of discrete data points equally-spaced in time. Then, the approximate entropy score is derived from the scalar time series. The approximate entropy score ApEn is defined by the equitation $ApEn(m,r,N)=\phi^m(r)-\phi^{m+1}(r)$. $\phi^m(r)$ is a classical entropy, and r is a predetermined parameter representing a noise filter.

There still is a need of an apparatus for applying at least one electric pulse to a living myocardial tissue in which an electric signal representing a present electric activity of the myocardial tissue is evaluated in such a way to trigger the at least one electric pulse at an optimum point in time that a desired resetting effect of the at least one electric pulses is achieved as an as low electric energy as possible.

SUMMARY OF THE INVENTION

The present invention relates to an apparatus for applying at least one electric pulse to a living myocardial tissue. The apparatus comprises an input configured to receive an electric signal representing a present electric activity of the myocardial tissue; a signal processor configured to process the electric signal to calculate a present permutation value of the electric signal in the state space and to only output a control signal when the calculated present entropy value of the electric signal is lower than a predetermined entropy threshold value; a pulse generator configured to generate the at least one electric pulse in response to the control signal; and an output configured to output the at least one electric pulse to the myocardial tissue.

Other features and advantages of the present invention will become apparent to one with skill in the art upon examination of the following drawings and the detailed description. It is intended that all such additional features and advantages be included herein within the scope of the present invention, as defined by the claims.

SHORT DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

The apparatus for applying at least one electric pulse to a living myocardial tissue according to the present invention comprises an input receiving an electric signal representing a present electric activity of the myocardial tissue; a signal processor processing the electric signal to determine a measure of the present complexity of the electric signal in the state space, and outputting a control signal when the complexity measure is lower than a predetermined complexity threshold value; a pulse generator generating the at least one electric pulse in response to the control signal; and an output outputting the at least one electric pulse to the myocardial tissue.

In the present invention, the complexity measure used for triggering the at least one electric pulse is not determined in the frequency space but in the state space. Even if, in the apparatus according to the present invention, a dominant frequency of the electric signal is additionally determined and evaluated, the complexity measure is not determined in the frequency space but in the state space. As a result, the complexity measure according to the present invention is more sensitive to the relevant complexity of the electric activity of the myocardial tissue, in that periods of low complexity are indicated more precisely and much quicker after the beginning of such periods than based on a complexity measure determined in the frequency space.

A quick determination of periods of low complexity in which the at least one electric pulse may be applied with a particularly low electric energy to achieve a desired result is a precondition to effectively use such a period for applying the at least one pulse to the myocardial tissue still having the low complexity measure, as these periods of low complexity may be quite short. Further, a high sensitivity for periods in which the complexity of the electrical activity of the myocardial tissue is low often allows for applying the at least one electric pulse much earlier than in case of a less sensitive complexity measure. Applying the electric pulse much earlier means terminating a life-threatening electric activity of the myocardial tissue like fibrillation much earlier. Further, the probability that the electric activity of the myocardial tissue is in fact of low complexity when the complexity measure is low so that the desired effect of the electric pulse will be achieved with a comparatively low electric energy is higher with a more sensitive complexity measure.

One reason for the higher sensitivity of the complexity measure according to the present invention determined in the state space may be that a length or period of the electric signal which has to be evaluated for determining the complexity measure may be much shorter than in case of a complexity measure being determined in the frequency space.

At least one electrode registering electric potentials or voltages at the myocardial tissue may be connected to the input of the apparatus according to the present invention, or the input may receive an ECG registered by other means.

The pulse generator of the apparatus according to the present invention may prepare for generating the at least one electric pulse prior to the control signal being provided by the signal processor. For example, a capacitor of the pulse generator may be charged as soon as an arrhythmic electric state of the myocardial tissue is noticed so that the at least one electric pulse may be generated by discharging the capacitor as soon as the control signal is present.

The output of the apparatus according to the present invention may be configured for connecting at least one electrode to apply the at least one electric pulse to the myocardial tissue. This electrode may in fact be the same electrode connected to the input of the apparatus for obtaining the electric signal representing the electric activity of the myocardial tissue. The electrodes for obtaining the electric signal and for applying the at least one electric pulse may be intra-corporal and/or extra-corporal electrodes when the myocardial tissue is the myocardium of a heart of a living animal or human being.

In the apparatus according to the present invention, the signal processor is configured to determine the present complexity measure such that it determines that the present complexity measure is below the complexity threshold value and outputs the control signal at a coincidence in time of at least 80%, preferably of at least 90% and more preferably of at least 95% with periods in which a calculated present permutation entropy $S_P$ of the electric signal is lower than a predetermined entropy threshold value.

It has been found that the present permutation entropy of the electric signal is a very well suited and sensitive complexity measure to determine those periods in which the at least one electric pulse should be applied to the myocardial tissue to have its desired effect at an as low electric energy as possible. It will, however, not be decisive whether the complexity measure is actually calculated as the present permutation entropy of the electric signal as long as essentially the same periods of the electric signal are sensed as an indication of a low complexity of the electric activity of the myocardial tissue in the state space. This does not only apply to the calculated permutation entropy as such but also to the permutation entropy calculated in the following way and using the following parameter settings.

Particularly, the present permutation entropy $S_P$ of the electric signal may be calculated as $$S_P = -\Sigma P_m \times \log(P_m)$$

Here, the sum is calculated for m=1, ... D!, and probabilities $P_m$ of motifs determined for series of N values of the electric signal sampled at intervals $\Delta T$. The probability $P_m$ is the number of occurrences of the respective one of the D! different motifs of D consecutive values separated by L values in the series of the N values divided by the total number of occurrences of all different motifs which is $(N-(D-1)\times L)$. In other words, for calculating the permutation entropy according to the above formula, each group of D consecutive values separated by L values within the N values of the electric signal is assigned to one of the D! different motifs. Then the numbers of occurrences of the different motifs are determined and normalized resulting in the probabilities $P_m$. The D! different motifs are assigned to the respective D consecutive values separated by L values of the electric signal by looking at the relative heights of the values and assigning integers 1 to D to theses values in the relative order of their heights. According this concept, the D consecutive values may display D! different motifs as the integers 1 to D may be arranged in D! different orders or patterns.

In the apparatus according to the present invention, the present permutation entropy of the electric signal is calculated using particularly settings of the parameters $\Delta T$, $L \times \Delta T$, D and $N \times \Delta T$. Typically, $\Delta T$ is not more than about 1 ms corresponding to a sample rate of 1,000 Hz. $L \times \Delta T$ is typically in a range from 0.1 ms to 250 ms, and $N \times \Delta T$ is typically in a range from 100 ms to 10 s. Preferably, $L \times \Delta T$ is in a range from 0.5 ms to 200 ms, and $N \times \Delta T$ is in a range from 125 ms to 2 s, more preferably, $L \times \Delta T$ is in a range from 1 ms to 100 ms, and $N \times \Delta T$ is in a range from 250 ms to 1 s. Most preferably, $L \times \Delta T$ is in a range from 20 ms to 50 ms, and $N \times \Delta T$ is in a range from 300 ms to 1 s. D is in a range from 2 to 6. Preferably, D is in a range from 3 to 5. More preferably, it is in a range from 3 to 4, and most preferably, D is 4.

Using these parameter settings, the present permutation entropy is a highly sensitive measure of the complexity of the electric activity of the myocardial tissue suitable for determining periods in which the myocardial tissue is highly susceptible to changing its electric activity in a desired way when the at least one electric pulse is applied, even if the at least one electric pulse has a comparatively low electric energy.

As already indicated above, the signal processor of the apparatus according to the present invention may be configured to additionally determine a dominant frequency of the electric signal. This dominant frequency may be compared to a predetermined frequency threshold value to determine whether the myocardial tissue displays a tachycardia or fibrillation to only apply the at least one electric pulse to the myocardial tissue when such a tachycardia or fibrillation is to be terminated. Particularly, the signal processor may only determine the present complexity measure of the electric signal and/or to only output the control signal when the dominant frequency of the electric signal is above the predetermined frequency threshold value. This frequency threshold value may, for example, be set to about 3 Hz for a tachycardia and to about 5 Hz for a fibrillation of the myocardial tissue.

Further, the signal processor of the apparatus according to the present invention may be configured to predetermine the complexity threshold value as the permutation entropy $S_P$ of a sinusoidal signal with the dominant frequency of the electric signal.

The dominant frequency determined by the signal processor of the apparatus according to the present invention may also be used to set the parameter $L \times \Delta T$ in calculating the present permutation entropy. For example, $L \times \Delta T$ may be in a range from 20 to 30% or about a quarter of the reciprocal value of the dominant frequency. Alternatively, the signal processor may be configured to determine an autocorrelation function of the electric signal. Then, $L \times \Delta T$ may be set in a range from 80 to 120% of the point in time of the first zero crossing or of the first local minimum of this autocorrelation function.

It is, however, also possible to set the parameter $L \times \Delta T$ to a fixed value of, for example, about 30 ms. This value, however, will also be in the above indicated ranges of $L \times \Delta T$ determined based on the dominant frequency or the autocorrelation function of the electric signal.

As already indicated above, the signal processor may be configured to determine the present complexity measure of the electric signal as the present permutation entropy $S_P$ itself. In other embodiments, the signal processor is configured to determine the present complexity measure of the electric signal as any suitable generalized present entropy, complexity or information measure of the electric signal based on symbolic sequences obtained from ordinal patterns and corresponding probabilities $P_m$ of motifs of the symbols. These measures include Renyi entropies of order q, where the entropy is calculated as $S_P(q)=(1-q)^{-1} \log (\Sigma(P_m)^q)$. A useful range of the order parameter q is from -12 to 12, preferably from -8 to 8 and more preferably from -4 to 4. In case of q approaching 1 the Renyi entropy converges to the permutation entropy $S_P$ as defined above.

Further, these measures include sums, differences and other functional expressions of Renyi entropies of different motif lengths D; and measures based on compression algorithms, such as the Lempel-Ziv algorithm and its variants, see U.S. Pat. Nos. 4,558,302, 4,464,650, 4,814,746. Here the sequence S of the symbols is decomposed into non-overlapping subsequences $S=S_1S_2S_3S_4 \ldots S_I$ such that each subsequence $S_k$ ($2 \leq k \leq I$) cannot be copied from the symbol sequence consisting of the concatenation of the first k−I subsequences $S_1S_2S_3S_4 \ldots S_{k-1}$. The Lempel-Ziv complexity is defined as the normalized number of subsequences I needed to represent the entire symbol sequence: I log(N)IN. It is known to those skilled in the art that the Lempel-Ziv complexity is equivalent to the permutation entropy $S_P$ which is a so-called Shannon entropy.

Further, the signal processor may be configured to determine the present complexity measure of the electric signal as a PCA-Entropy computed by generating a trajectory matrix from the electric signal, computing singular value decomposition of the trajectory matrix, normalizing the singular values such that their sum equals one, and computing the Shannon Entropy from the normalized singular values.

The applicable complexity measures also include the above described entropy measures applied to other transformations of the electric signal $e(t_k)$ (with $t_k=k\Delta T$) into a symbol sequence $s(t_k)$ like Transformations based on static partitions: these symbolic descriptions are based on partitions of the interval containing all values of the electric signal ($e(t_k)$, $1 \leq k \leq N$). The interval borders are defined by two numbers a and b such that $a<e(t_k)<b$ for $1 \leq k \leq N$. The partition is defined by m numbers $c_1, c_2, c_3, \ldots, c_m$ with $a<c_1<<c_3< \ldots <c_m<b$. The m+1 distances $c_1-a$, $c_2-c_1$, $c_3-c_2 \ldots$, $b-c_m$ can be identical or not. A symbol is assigned to each subinterval (i.e., to each of the intervals [a, $c_1$), [$c_1$, $c_2$), [$c_2$, $c_3$), $\ldots$ [$c_m$, b)) and each element of the electric signal $e(t_k)$ is transformed into the symbol of its containing subinterval.

Dynamic partitions: here the symbols are assigned to differences of succeeding values of the electric signal, i.e., to $e(t_k)-e(t_{k-1})$, $2 \leq k \leq N$. Then the interval containing the values $e(t_k)-e(t_{k-1})$, $2 \leq k \leq N$, is partitioned into subintervals of identical or non-identical size and the symbol sequence is constructed in accordance to this partition.

Combinations of static and dynamic partitions for transforming the electrical signal into a symbol sequence.

Transformations based on partitions in reconstructed state space: The electric signal ($e(t_k)$, $1 \leq k \leq N$) is used to construct D-dimensional delay vectors [$e(t_k)$, $e(t_k-L\Delta T)$, $\ldots$, $e(t_k-(D-1)L\Delta T)$] specifying points in a D-dimensional delay reconstruction space. Symbols are associated to each point and each signal value $e(t_k)$ by partitioning the D-dimensional reconstruction space.

The applicable complexity measures also include low values of the variance of the residuals of fitted low-dimensional (prediction) models including ARMA-type linear prediction models or low-dimensional nonlinear deterministic systems (defined in a reconstructed state space); and low number of principal components that explain a high percentage (of at least 95%) of the variance of the embedded ECG-signal of the preceding window (PCA=principle component analysis).

Alternatively or additionally to the above described preprocessing of the electric signal, the signal generator may filter, compress or transform the electric signal within the state space prior to determining the present complexity measure of the electric signal. For example, the signal processor may filter the electric signal to reduce it to a certain frequency range. The electric signal filtered in such a way will nevertheless be in the state phase and it will be evaluated in the state phase after filtering. Another example is low pass filtering the electric signal in such a way that the sample of the electric signal taken at the $\Delta T$ intervals will be average values of the original signals over these $\Delta T$ intervals. Yet another feature will be transforming the electric signal from a linear to a logarithmic scale or vice versa.

The predetermined complexity threshold value or entropy threshold value may be set to a fixed value. More preferably, however, the signal processor determines the complexity or entropy threshold value by determining a minimum value of the present complexity or entropy measures over a period of time and setting the complexity or entropy threshold value to a predetermined percentage of the minimum value. Particularly, the predetermined percentage of the minimum value to which the predetermined complexity or entropy value is set is in a range from 103 to 120%. Preferably, it is in a range from 105 to 110%.

The signal processor of the apparatus according to the present invention may comprise an A/D converter to sample the electric signal at the intervals $\Delta T$. The actual signal processing may then be digital, i.e. performed by a computer program implemented in hardware or software.

The electric signal may particularly be an ECG signal or any other voltage signal.

The electric signal may already be a digital signal when provided to the signal processor via the input of the apparatus according to the present invention. Even then, it will be regarded as an electric signal here as it is representing the electric activity of the myocardial tissue.

In one embodiment of the apparatus of the present invention, the signal processor determines the present complexity measures of a plurality of electric signals provided by a plurality of sensors sensing the present electric activity of the myocardial tissue in a plurality of areas of the myocardial tissue. The signal processor may then output the control signal when the present complexity measures of at least a predetermined fraction of the plurality of electric signals are lower than the predetermined complexity threshold value.

The plurality of electric signals may generally consist of four to twenty electric signals. Often six to ten electric signals will be evaluated. The signal processor may, for example, output the control signal when the present complexity measures of all but at maximum of three electric signals or two electric signals or only one electric signal of the plurality of electric signals are/is lower than the predetermined complexity threshold value. At least, more than half of the present complexity measures should be lower than the predetermined complexity threshold value, when the control signal is output.

Preferably, the plurality of sensors sense the present electric activity of the myocardial tissue in a plurality of equally spaced areas of the myocardial tissue. Particularly, the plurality of sensors may be arranged on a virtual ring enclosing the myocardial tissue which typically will be the heart of a patient.

The apparatus according to the present invention may be used to supply one single electric pulse for terminating a fibrillation of the myocardial tissue by an electric shock at a most appropriate point in time so that the electric energy of the electric pulse may be comparatively low without endangering the desired termination of the fibrillation.

Alternatively or additionally, the apparatus according to the present invention may be used for applying a group of electric pulses for terminating a fibrillation of the myocardial tissue by low energy anti-fibrillation pacing once again at a most appropriate point in time to terminate the fibrillation with an as low overall electric energy as possible. In this embodiment of the apparatus according to the invention, at least the first electric pulse of the group of electric pulses will be applied during a period of low complexity of the activity of the myocardial tissue as indicated by the low value of the complexity measure determined in the state space.

Even further or alternatively, the apparatus according to the present invention may be used to apply a train of electric pulses for terminating a tachycardia of the myocardial tissue by anti-tachycardia pacing. Here as well, the first electric pulse of the train of the electric pulses is applied when the complexity of the electric activity of the myocardial tissue is low as indicated by the present complexity measure calculated in the state space.

Figure 1:
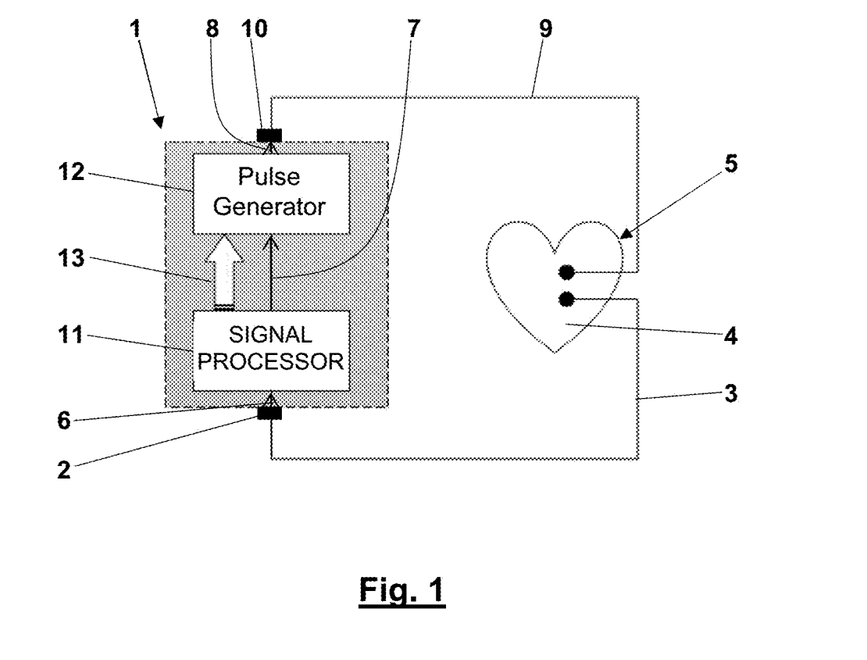
FIG. 1 is a schematic diagram of the apparatus according to the present invention.

Referring now in greater detail to the drawings, the apparatus 1 schematically depicted in FIG. 1 comprises an input 2. An electrode 3 connected to the input 2 senses electrical activity of a myocardial tissue 4, i.e. of a myocardium of a heart 5. Via the electrode 3 the input 2 receives an electric signal representing the electric activity of the myocardial tissue 4. The electric signal 6 is processed by a signal processor. The signal processor processes the electric signal to determine whether the electrical activity of the myocardial tissue 4 displays an abnormality, like for example a fibrillation or tachycardia. If such an abnormality is detected, the signal processor sends a startup signal 7 to a pulse generator 12 of the apparatus 1. Upon receipt of the startup signal 7 the pulse generator 12 prepares for generating at least one electric pulse 8 which will be applied via a further electrode 9 to the myocardial tissue 4 via an output 10 of the apparatus 1. The signal processor 11 further determines periods in which the myocardial tissue 4 is particularly susceptible to the electric pulses 8 for terminating the present abnormality of its electric activity. In these periods, the electric activity has a particularly low complexity. These periods are indicated by the signal processor 11 to the signal generator 12 by a control signal 13. When started up and receiving the control signal 13, the pulse generator 12 generates the at least one electric pulse 8.

Figure 2:
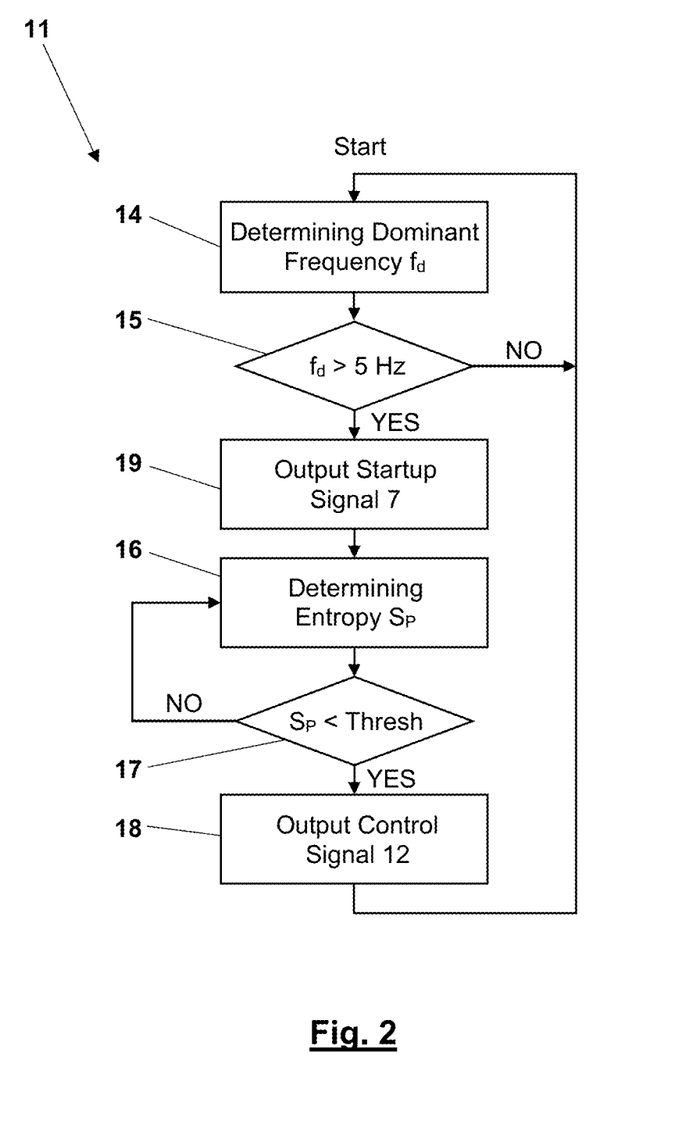
FIG. 2 is block diagram of the signal processor of the apparatus according to FIG. 1.

The block diagram of FIG. 2 shows how the signal processor 11 works. In a processing module 14 the signal processor 11 determines a dominant frequency $f_d$ of the electric signal. In a decision module 15 the signal processor 11 decides whether the dominant frequency $f_d$ is above 5 Hz or not. If it is not above 5 Hz, the signal processing returns to the processing module 14. Otherwise, the startup signal 7 is output to the pulse generator by a signaling module 19, as a dominant frequency above 5 Hz is indicative of a fibrillation of the myocardial tissue. In a processing module 16, the signal processor 11 determines the permutation entropy $S_P$ of the electric signal. In a following decision module 17, the signal processor determines whether the permutation entropy is below an entropy threshold value. If not, the signal processing returns to the processing module 16. Otherwise, the control signal 12 is output by a signaling module 18, and then the signal processing returns to start.

The processing module 16 according to FIG. 2 works as follows. The electric signal is sampled at intervals $\Delta T$. For calculating the present permutation entropy, N consecutive sampled values of the electric signals are evaluated. The evaluation includes determining the motif displayed by each number of D consecutive values of the electric signal within the series of N values. Whether a particular motif is displayed by D consecutive values depends on the sequence of the relative heights of these values.

Figure 3A:
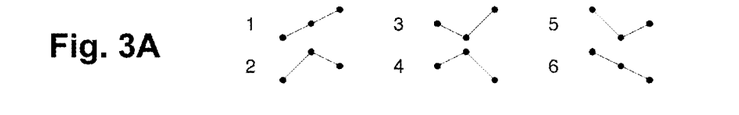
FIG. 3A shows the different motifs of length D=3.
Figure 3B:
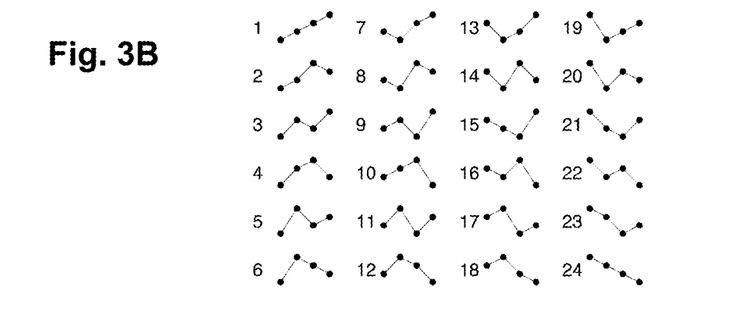
FIG. 3B shows the different motifs of length D=4.
Figure 3C:
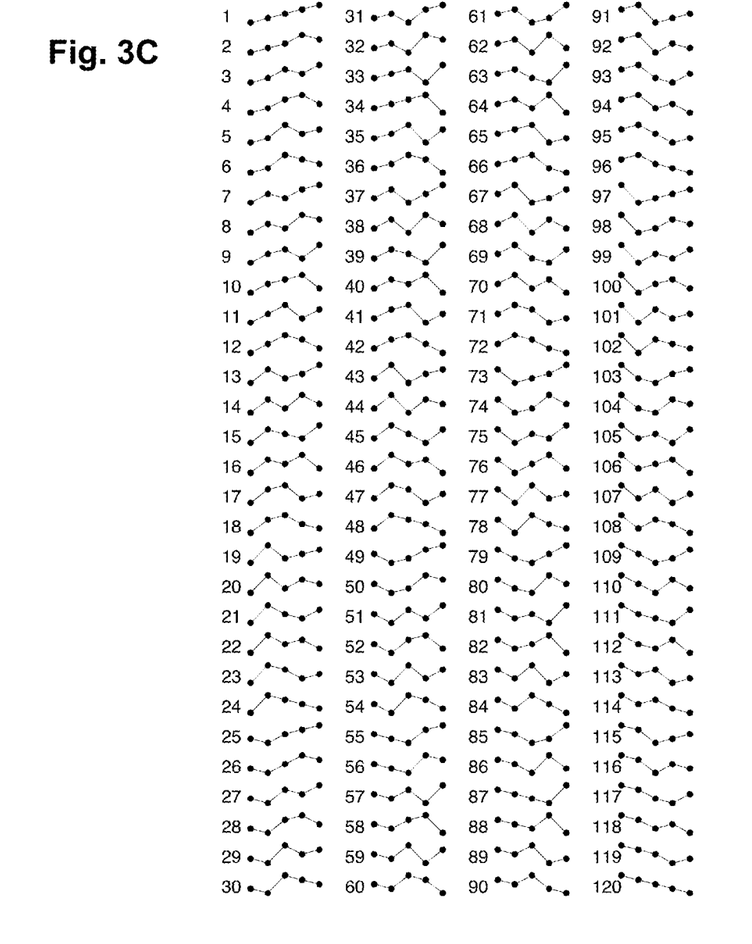
FIG. 3C shows the different motifs of length D=5.

FIG. 3A shows the six different motifs for a length D=3 starting with a continuously increasing height of the values. The total number of the motifs is D!=6. FIG. 3B shows the D!=24 motifs of the length D=4, and FIG. 3C shows the D!=120 motifs of the length D=5. Which of the D! motifs is displayed by the consecutive values of the electric signal is determined for each of the N−(D−1)×L starting points within the series of N values of the electric signal. The permutation entropy is calculated from the numbers of occurrences of the individual motifs as $$S_P = -\Sigma P_m \times \log(P_m) \text{ for } m=1, \ldots, D!,$$

wherein $P_m$ is the number of occurrences of the respective motif divided by (N−(D−1)×L). The permutation entropy is compared to a entropy threshold value. This entropy threshold value may be set according to a minimum value of the present permutation entropy over a previous period. For example, the entropy threshold value may be 110% of the minimum value.

Figure 4A:
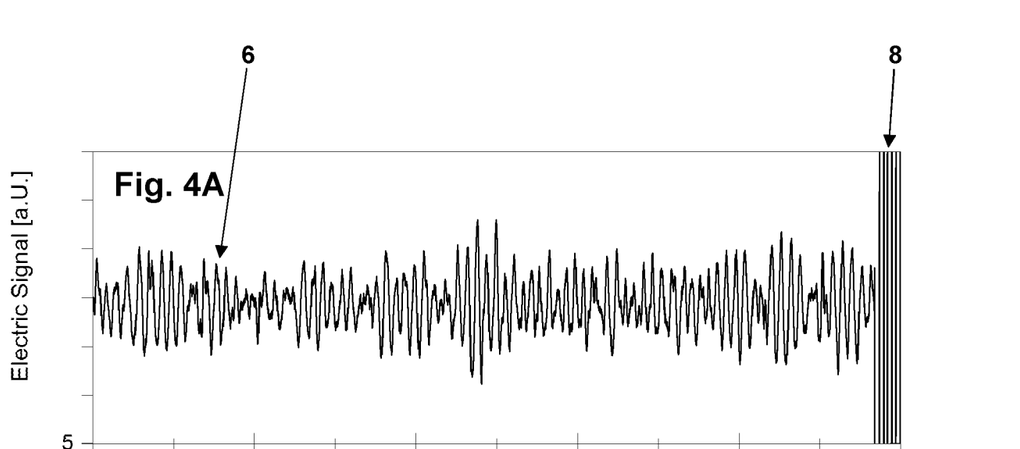
FIG. 4A shows an electric signal representing an electric activity of a myocardial tissue.
Figure 4B:
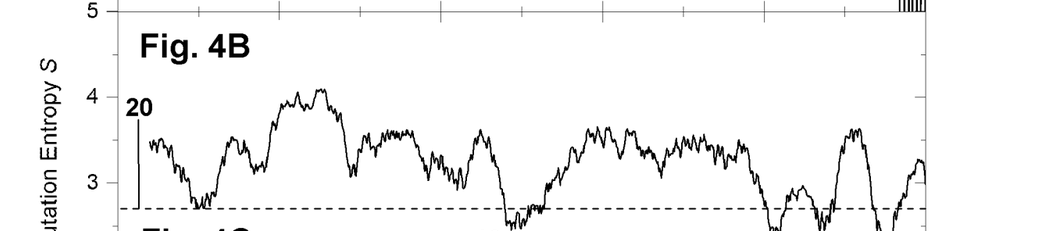
FIG. 4B shows a present permutation entropy $S_P$ of the electric signal.
Figure 4C:
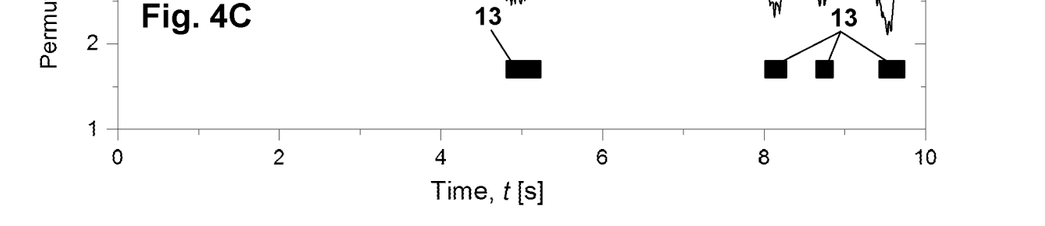
FIG. 4C shows time periods in which the permutation entropy $S_P$ is below an entropy threshold value.

FIG. 4A shows an exemplary electric signal 6. FIG. 4B shows the corresponding present permutation entropy $S_P$ calculated as described above and compared to the entropy threshold value 20. FIG. 4C indicates the periods of time in which the control signal 13 is output by the signal processor 11 according to FIG. 1 as the present permutation entropy $S_P$ is below the entropy threshold value 20. The far right period of the control signal 13 is used here to trigger a sequence of electric pulses 8 from the pulse generator 12 according to FIG. 1 which are seen in the electric signal 6.

Many variations and modifications may be made to the preferred embodiments of the invention without departing substantially from the spirit and principles of the invention. All such modifications and variations are intended to be included herein within the scope of the present invention, as defined by the following claims.

We claim:

1. An apparatus for applying at least one electric pulse to a living myocardial tissue, the apparatus comprising:
   an input configured to receive an electric signal representing a present electric activity of the myocardial tissue;
   a computing device that comprises a processor and memory;
   a plurality of machine instructions stored in memory, wherein when executed, the machine instructions causes the processor to at least:
   determine that a dominant frequency of the electric signal is above a predetermined frequency threshold;
   in response to the dominant frequency being above the predetermined frequency threshold, calculate a present permutation entropy value of the electric signal in the state space, wherein a control signal is generated for a pulse generator when the calculated present permutation entropy value of the electric signal is lower than a predetermined entropy threshold value,
   wherein the present permutation entropy value of the electric signal is calculated as a present permutation entropy $S_p$ according to $$S_p = -\Sigma P_m \times \log(P_m) \text{ for } M=1, \ldots, D!$$

for a series of N values of the electric signal sampled at intervals $\Delta T$,
   wherein $P_m$ is a number of occurrences of a respective one of D! different motifs of D consecutive values separated by L values in the series of the N values divided by the total number of occurrences of all different motifs which is (N (D−1) x L),
   wherein L x $\Delta T$ is in a range from 0.1 ms to 250 ms and N x $\Delta T$ is in a range from 100 ms to 10 s, and
   wherein D is in a range from 2 to 6;
   cause the pulse generator to generate the at least one electric pulse in response to the control signal being generated; and cause a generation of an output to the at least one electric pulse to the myocardial tissue.

2. The apparatus of claim 1, wherein the machine instructions further causes the processor to determine the present entropy value of a plurality of electric signals provided by a plurality of sensors configured to sense the present electric activity of the myocardial tissue in a plurality of areas of the myocardial tissue; and wherein the signal processor is configured to output the control signal when the present entropy values of at least a predetermined fraction of the plurality of electric signals are lower than the predetermined entropy threshold value.

3. The apparatus of claim 2, wherein the plurality of electric signals consist of four to twenty electric signals; and wherein the signal processor is configured to output the control signal when the present entropy values of all but at maximum of three electric signals of the plurality of electric signals are lower than the predetermined entropy threshold value.

4. The apparatus of claim 2, wherein the plurality of sensors are configured to sense the present electric activity of the myocardial tissue in a plurality of equally spaced areas of the myocardial tissue.

5. The apparatus of claim 2, wherein the plurality of sensors are configured to be arranged on a virtual ring enclosing the myocardial tissue.

6. The apparatus of claim 2, wherein the pulse generator is configured to generate electric pulses selected from:
single electric pulses for terminating a fibrillation of the myocardial tissue by an electric shock and
groups of electric pulses for terminating a fibrillation of the myocardial tissue by low energy anti-fibrillation pacing and
trains of electric pulses for terminating a tachycardia of the myocardial tissue by anti-tachycardia pacing.

7. The apparatus of claim 1, wherein L x ΔT is in a range from 0.5 ms to 200 ms and N x ΔT is in a range from 125 ms to 2.0 s.

8. The apparatus of claim 1, wherein D is in a range from 3 to 5.

9. The apparatus of claim 1, wherein the machine instructions further causes the processor to output the control signal in an instance in which the dominant frequency $f_d$ of the electric signal is above the predetermined frequency threshold value.

10. The apparatus of claim 1, wherein the machine instructions further causes the processor to predetermine the entropy threshold value as the permutation entropy $S_p$ of a sinusoidal signal with the dominant frequency of the electric signal.

11. The apparatus of claim 1, wherein L x ΔT is in a range from 20 to 30% of 1/f, wherein $f_d$ is the dominant frequency.

12. The apparatus of claim 1, wherein the machine instructions further causes the processor to determine an autocorrelation function of the electric signal, and wherein L x ΔT is in a range from 80 to 120% of the first zero crossing or local minimum of the autocorrelation function.

13. The apparatus of claim 1, wherein the machine instructions further causes the processor to filter, compress or transform the electric signal within the state space prior to determining the present permutation value of the electric signal.

14. The apparatus of claim 1, wherein the machine instructions further causes the processor to determine the entropy threshold value by determining a minimum value of the present entropy values within a preceding period of time and setting the entropy threshold value at a predetermined percentage of the minimum value, wherein the predetermined percentage is in a range from 103 to 120%.

15. The apparatus of claim 1, wherein the processor comprises an A/D converter to sample the electric signal at the intervals T.

16. The apparatus of claim 1, wherein the electric signal is a voltage signal or an ECG signal.

* * * * *